United States Patent [19]

Hon

[11] Patent Number: 5,511,546
[45] Date of Patent: Apr. 30, 1996

[54] FINGER APPARATUS FOR MEASURING CONTINUOUS CUTANEOUS BLOOD PRESSURE AND ELECTROCARDIOGRAM ELECTRODE

[76] Inventor: Edward H. Hon, 11 Bradbury Hills Rd., Bradbury, Calif. 91010

[21] Appl. No.: 124,101

[22] Filed: Sep. 20, 1993

[51] Int. Cl.⁶ ..................................................... A61B 5/02
[52] U.S. Cl. .......................... 128/633; 128/639; 128/666; 128/667
[58] Field of Search ..................... 128/633, 639, 128/666, 667, 672, 686, 689

[56] References Cited

U.S. PATENT DOCUMENTS

| | | | |
|---|---|---|---|
| 3,482,565 | 12/1969 | Gowen | 128/667 |
| 4,332,258 | 6/1982 | Arai et al. | 128/666 |
| 4,653,500 | 3/1987 | Osada et al. | 128/639 |
| 4,883,055 | 11/1989 | Merrick | 128/666 |
| 4,915,116 | 4/1990 | Hasebe et al. | 128/666 |
| 5,025,792 | 6/1991 | Hon et al. | 128/672 |
| 5,035,243 | 7/1991 | Muz | 128/633 |
| 5,065,749 | 11/1991 | Hasebe et al. | 128/666 |
| 5,077,476 | 12/1991 | Rosenthal | 128/633 |
| 5,086,229 | 2/1992 | Rosenthal et al. | 128/633 |
| 5,125,403 | 6/1992 | Culp | 128/633 |
| 5,247,931 | 9/1993 | Norwood | 128/633 |
| 5,275,159 | 1/1994 | Griebel | 128/633 |
| 5,313,940 | 5/1994 | Fuse et al. | 128/633 |

FOREIGN PATENT DOCUMENTS

| | | | |
|---|---|---|---|
| 0204459 | 12/1986 | European Pat. Off. | 128/633 |
| 2003965 | 3/1992 | European Pat. Off. | 128/633 |
| 2635221 | 2/1978 | Germany | 128/666 |
| 3938759 | 5/1991 | Germany | 128/633 |
| 4261646 | 9/1992 | Japan | 128/633 |

*Primary Examiner*—Krista M. Zele
*Attorney, Agent, or Firm*—Lewis Anten; Amedeo Ferraro

[57] ABSTRACT

Apparatus for continuously and non-invasively monitoring and measuring various biochemical and biophysical functions through the finger of a patient. The apparatus of the present invention comprises a highly stable finger attachment device for maintaining one or more sensing monitors such as a pressure transducer (or similar pressure measuring device) or electrode against the fleshy part of the finger. The increased stability of the finger attachment device is accomplished by taking advantage of the anatomical structure of the middle phalanx of a finger. The finger attachment device has an upper and a lower arm attached to each other by a hinge, so that when closed, protuberances from each arm fit snugly into the natural concavities of the middle phalanx thereby holding the finger firmly and providing a high level of mechanical stability and thus reducing pulse waveform distortion and any other "noise" or motion artifact due to instability. The stability of the finger attachment assembly permits the use of a sensing monitor that is pressure sensitive such as an isolation ring pressure transducer and also an electrocardiograph electrode for taking an electrocardiogram through the finger of a patient.

5 Claims, 6 Drawing Sheets

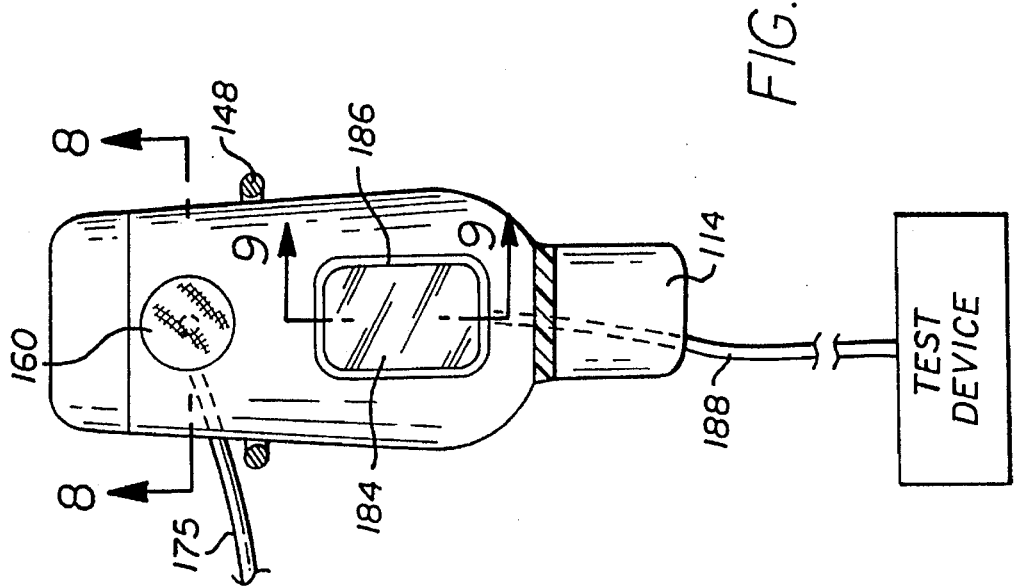
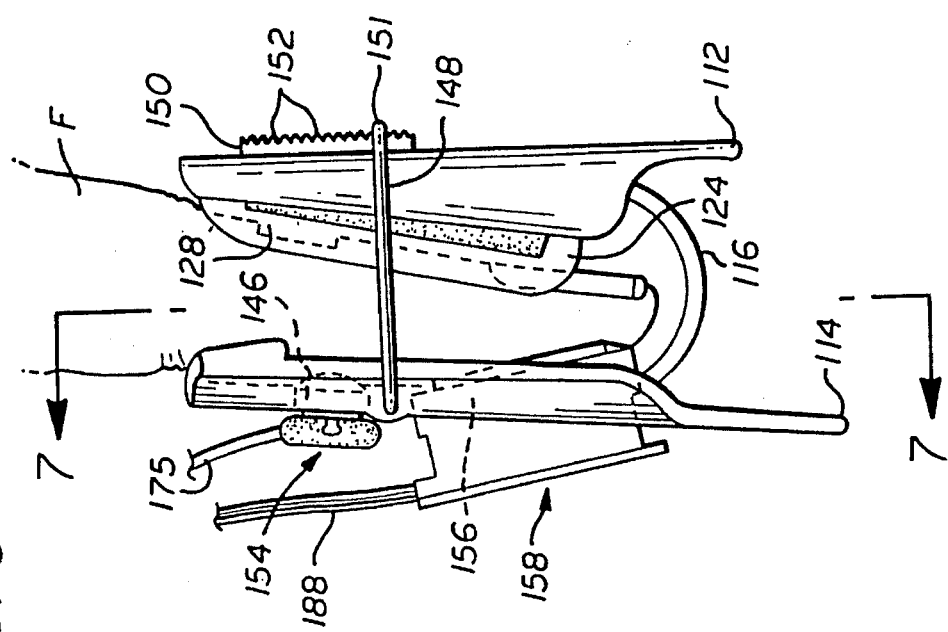

1

FINGER APPARATUS FOR MEASURING CONTINUOUS CUTANEOUS BLOOD PRESSURE AND ELECTROCARDIOGRAM ELECTRODE

BACKGROUND OF THE INVENTION

1. Field of the Invention

This invention relates to medical monitoring apparatus, and more particularly to a non-invasive apparatus for continuously monitoring and measuring various biophysical functions through tile finger of a patient.

2. Description of the Related Art

Non-invasive monitoring of biochemical and biophysical functions is largely focused on obtaining data from the fingers by coupling various biosensors capable of acquiring oxygen and carbon dioxide tension, oxygen saturation, PH and other measurements from the patient's skin. Biophysical measurements such as blood flow and blood pressure are also obtained. The measurement of blood pressure based on repetitive evaluation of the cutaneous blood pressure fluctuation patterns of minute branches of larger arteries reflects the arterial blood pressure of the general circulation since the latter is the source of the former.

The continuous monitoring of blood pressure patterns over extended periods of time is often needed in the evaluation of circulatory function, and is useful for hypertension studies and for obtaining records of circulation in the peripheral systems, particularly of the limbs, fingers and toes. Many devices currently used for patient monitoring are frequently attached for hours and/or days at a time.

To obtain accurate measurements of these biophysical and biochemical functions, the stability of the coupling between sensor and patient is of paramount importance. If instability is present, motion artifacts or "noise" may also contaminate the data that it is rendered inaccurate and unreliable.

At present, one of the most widely used measurements is skin oxygen saturation which is determined by analyzing the oxygen content of the blood flowing into a finger using optical methods such as infra-red radiation and receiving sensors. These sensors are held against the finger by "clothespin" type attachment devices where the retention element is a metal or plastic spring. Since finger size is not uniform, compensation is provided by lining the arms of the device with sponges or air-sacks. While the addition of these materials add to the stabilizing of the attachment system, they absorb mechanical energy so that the fidelity of the blood flow pulse shape is compromised. Furthermore, the skin-sensor interface is not completely stabilized since the anatomy of the finger is tapered as is the aperture provided by the "clothespin" attachment device.

The measurement of blood pressure and associated pressure pulse waveform demands a more stable coupling system. In the past, gantry type systems have been used with an isolation ring pressure transducer held firmly against the finger-tip with the aid of a longitudinally directed spring as disclosed in U.S. Pat. No. 5,025,792 issued Jun. 25, 1991 to Hon et al. Adjustment to individual patient's finger size was provided by a screw mechanism. Since the application system to a large extent was "customized" to the patient's anatomy the stability achieved was greater than that of a "clothespin" attachment device. However, since the adjustment to an individual patient's finger required the in-line insertion of a spring, some distortion of pressure pulse waveform was an inherent problem.

Stability of the attachment device is also of utmost importance when the sensor is an electrode. In medicine, electrodes are widely used for recording the electrocardiogram of a patient and may be grouped into two major types. The first group is the reusable electrocardiographic (ECG) electrodes which are attached to the patient's extremities with latex straps and to the patient's body with suction cups. The second group is the single use ECG electrodes which are attached to the patient's extremities with adhesive material. The conductive material of the reusable electrodes is usually metallic such as silver or nickel silver and is cleansed between uses with an antiseptic agent such as alcohol. The conductive material of the single use ECG electrodes is usually a silver-silver chloride composite or silver-silver chloride alone or some solid state ionic conducting material. A conductive gel or paste covers the surface of the electrode which is isolated from the patient by a sponge.

However, both types of ECG electrodes have disadvantages. The reusable type are inconvenient to use and can only be used for short intervals. With exercise the suction cups become loose and electrical contact is lost. Furthermore, the metallic nature of the electrode material is not as compatible with human tissue as a metallic salt electrode such as silver-silver chloride. If silver is used as the electrode material, chloride ions from the sodium chloride present in body perspiration gradually will deposit on the silver reducing the effective surface area and thus increasing electrode resistance. Additionally the direct metal-to-skin electrode contact generates electrical "noise" with skin movement against the electrode resulting in motion artifacts in the record rendering the data obtained inaccurate and unreliable.

These disadvantages are largely eliminated by the single use electrode where a silver-silver chloride electrode is indirectly coupled to the patient by a gel-salt bridge and the electrode is attached to the patient's body with an adhesive backed sponge disk. However, this type of electrode often encounters a problem with the adhesion during initial attachment if the patients skin is damp. This problem is increased in some patients during various exercise tests used for monitoring cardiac function. This is especially true in "sports" medicine where athletes are exercised to maximum limits. One other problem with the adhesive type electrode is an allergic reaction to the adhesive material.

Therefore, there exists a need for a highly stable attachment device used to couple sensing monitors to a patient for a prolonged period without encountering the noise and motion artifacts experienced by the attachment devices of the past.

SUMMARY OF THE INVENTION

The present invention provides apparatus for continuously and non-invasively monitoring and measuring various biochemical and biophysical functions through the finger of a patient. The apparatus of the present invention comprises a highly stable finger attachment device for maintaining one or more sensing monitors such as a pressure transducer (or similar pressure measuring device) or electrode against the fleshy part of the finger. The increased stability of the finger attachment device is accomplished by taking advantage of the anatomical structure of the middle phalanx of a finger. This bony structure is essentially a cylinder which is gently flared at both ends, so that it presents a longitudinal concavity when viewed from the side. The finger attachment device has an upper and a lower arm attached to each other by a hinge, so that when closed, protuberances from each arm fit snugly into the natural concavities of the middle phalanx thereby holding the finger firmly and providing a high level of mechanical stability and thus reducing pulse waveform distortion and any other "noise" or motion artifact due to instability.

The stability of the finger attachment assembly permits the use of a sensing monitor that is pressure sensitive such as an isolation ring pressure transducer, to be placed in a fixed position on an arm of the assembly opposite a supporting plate, so that a uniform aperture is presented to the finger-tip regardless of its size, since the coupling is made of soft, deformable tissue. In this situation there is no need for a spring to compensate for finger size and/or tissue variations.

A small portion of cutaneous tissue is isolated from the surrounding tissue by the isolation ring surrounding the active surface of the transducer and pressing against the tissue. This isolation ring projects above the active measuring surface of the strain gauge and serves to isolate the tissues and reduce noise emanating from adjacent tissue. Further the isolation ring, which in the preferred embodiment is larger than the active surface of the pressure transducer, causes the portion of the cutaneous tissue to protrude into the opening fortified by the isolation ring and the pressure transducer into the shape of a dome, rather than a flat surface. The minute blood pressure pulsations in this protruding dome of isolated cutaneous tissue are measured with a pressure transducer whose active measuring surface is tangentially oriented to the dome of the isolated cutaneous tissue.

In its simplest form the aforesaid protuberances of the finger attachment assembly are passive, i.e. they do not possess any biosensing function. However, they can be constructed in such a manner so that they can be used as sensors, such as electrodes to acquire electrocardiographic signals.

The apparatus of the present invention utilizes an improved electrocardiographic (ECG) electrode that overcomes all the above-mentioned problems of the prior electrodes and possesses the electrical advantages of a silver-silver chloride system without the adhesion problems. This is of importance, especially during exercise where the adhesive system may weaken. With the electrode of the present invention, the increased production of electrolyte-rich body fluids enhances the electrolytic efficiency of the conductive gel bridge without lessening patient skin contact since the integrity of the skin-electrode coupling is dependant on mechanical coupling rather than an adhesive one.

Furthermore, the ECG electrode is so constructed that it is reusable. Cross-infection is largely eliminated by the use of an antiseptic conductive gel between the patient and the electrode. Additionally, between uses, the electrode assembly can be immersed in an antiseptic solution, without compromising electrical performance.

In patient use an electrode can be attached to a finger of the left hand and the other to a finger of the right hand. The resultant electrocardiogram is equivalent to the widely used left arm-right arm lead system. If the ECG system requires an "indifferent" or "ground" electrode, a ring electrode can be placed on another finger or on the same finger a distance apart (e.g. back and front). Such a ring electrode system provides a simple convenient easy-to-use method of obtaining a single lead ECG, moreover, it is especially useful for continuous monitoring of beat-to-beat rate and cardiac arrhythmia detection during diagnostic procedures and intensive care monitoring.

Additionally, the addition of infra-red sensors to the attachment device would provide a simple method to obtain blood flow data. Mechanical stability is also important for other biochemical and/or biophysical skin measurements all would provide more accurate data when obtained with the described biosensor attachment device.

OBJECTS OF THE PRESENT INVENTION

It is an object of the present invention to provide a finger attachment device that is highly stable when attached to a finger.

It is another object of the present invention to provide a finger attachment device for holding one or more sensing monitor devices for monitoring and measuring various biophysical functions of the patient.

It is a further object of the present invention to provide an apparatus for obtaining an electrocardiogram from the finger of a patient.

It is still a further object of the present invention to provide a reusable electrode mechanically coupled to the skin where increased production of electrolyte-rich body fluids enhances the electrolytic efficiency of the conductive gel bridge without lessening patient skin contact.

It is another object of the present invention to provide all apparatus for obtaining blood pressure measurements which do not require immobility of the patient and which provide a continuous, non-invasive blood pressure measurement.

It is yet another object of the present invention to provide a system that is inexpensive to manufacture and easy to use in association with equipment presently widely used by physicians.

It is also another object of the present invention to provide an easily attached stable transducer support for easily and quickly attaching the device to the patient.

These and other objects of the present invention will become apparent from a review o f the accompanying drawings and the detailed description of the drawings.

BRIEF DESCRIPTION OF THE DRAWINGS

FIG. 6 is a bottom plan view of the finger monitoring device of the present invention.

FIG. 7 is an elevational side view of the finger monitoring device of the present invention.

DETAILED DESCRIPTION OF THE DRAWINGS

1. The Prior Art

Figure 1:
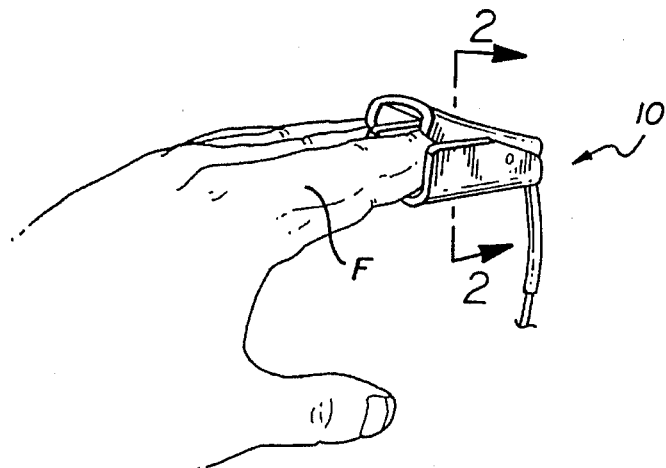
FIG. 1 is an elevational side view of a first prior art device.
Figure 2:
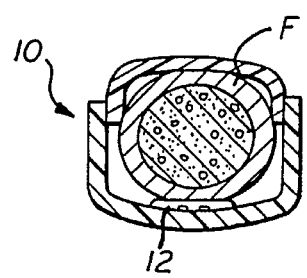
FIG. 2 is a cross sectional view taken along lines 2—2 of FIG. 1.

Referring to FIGS. 1–4, two finger holder assemblies of the prior art are shown. In FIGS. 1 and 2 a "clothes pin" type finger attachment assembly 10 is shown with infra-red radiation and receiving sensors 12 that are held against the finger F. Since finger size is not uniform, the finger moves around within the finger attachment assembly 10 and creates noise to interfere with true monitoring. The skin-sensor interface is not completely stabilized since the anatomy of the finger F is tapered as is the aperture for containing the finger F in the assembly 10.

Figure 3:
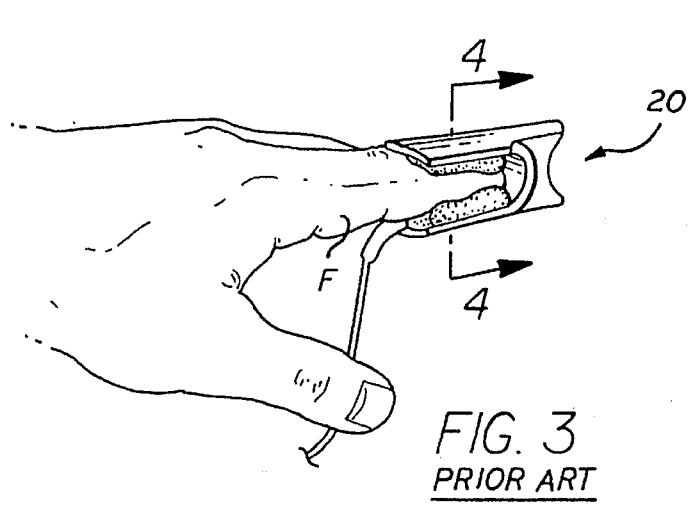
FIG. 3 is an elevational side view of a second prior art device.
Figure 4:
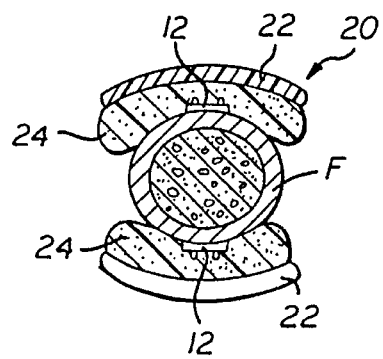
FIG. 4 is a cross sectional view along lines 4—4 of FIG. 3.

In FIGS. 3 and 4, a second finger attachment assembly 20 of the prior art provides compression by lining the arms 22 of the finger attachment assembly 20 with sponges or air sacks 24. While the addition of these materials adds to the stabilization of the finger attachment assembly 20 to the finger F, the sponge or air sack 24 absorb mechanical energy so that the fidelity of the blood flow pulse is compromised.

2. The Present Invention

Figure 13:
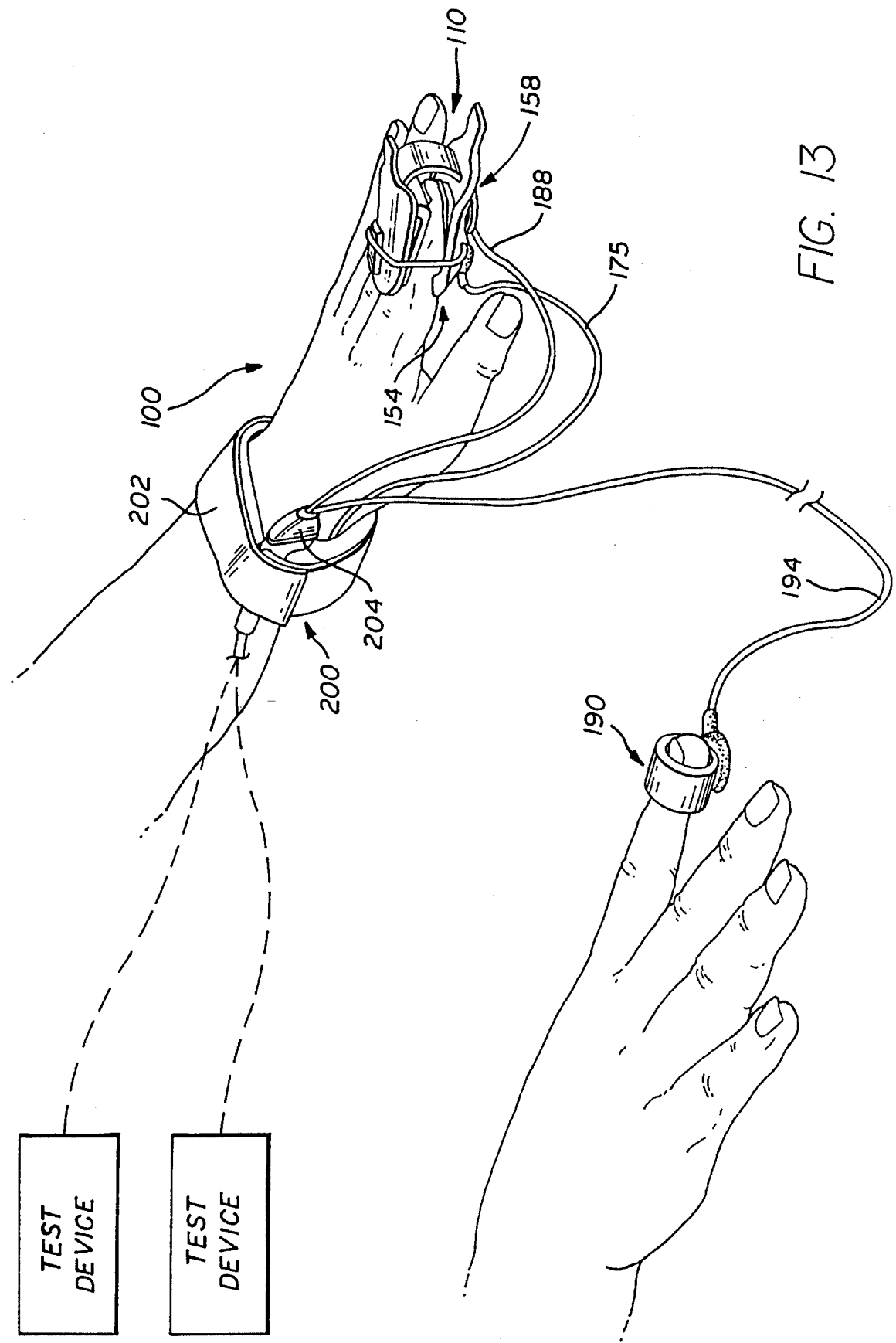
FIG. 13 is a perspective view of the finger monitoring device of the present invention worn by a patient.

Referring to FIGS. 13, the preferred embodiment of the monitoring apparatus 100 of the present invention is shown. The monitoring apparatus 100 consists of a finger attachment assembly 110, a first sensing monitor assembly 154, a second sensing monitor assembly 158, a third sensing monitor assembly 190 and wrist securing assembly 200.

Figure 5:
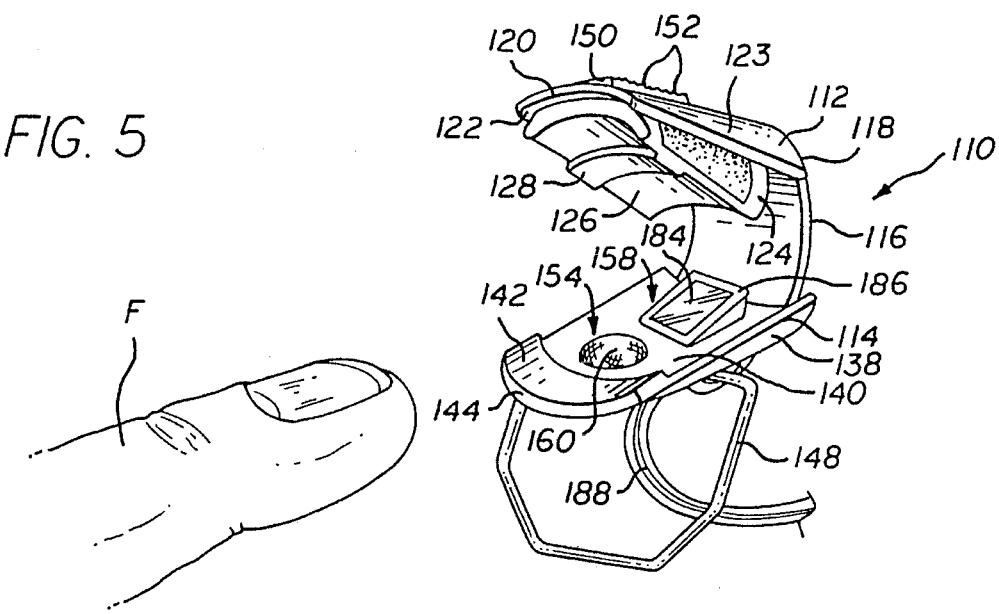
FIG. 5 is a perspective side view of the finger monitoring device of the present invention.

Referring to FIG. 5, the finger attachment assembly 110 consists of an upper arm 112 and a lower arm 114 for clasping the finger F of the user. The upper arm 112 and the lower arm 114 are connected by a living hinge 116 made of a flexible plastic: material. In the preferred embodiment, the living hinge 116 is approximately 1 ¼ inches long and approximately ¾ inches wide.

The upper arm 112 has a distal end 118, a proximal end 120, has a concave interior surface 122 that corresponds and conforms to the external curvature of a finger F and a convex exterior surface 123. The upper arm 112 has an overall length of approximately 2 inches, an overall width of approximately 1 ¼ inches and is about ¼ inches thick. In the preferred embodiment the upper arm 112 is formed of a substantially rigid plastic material.

Figure 11:
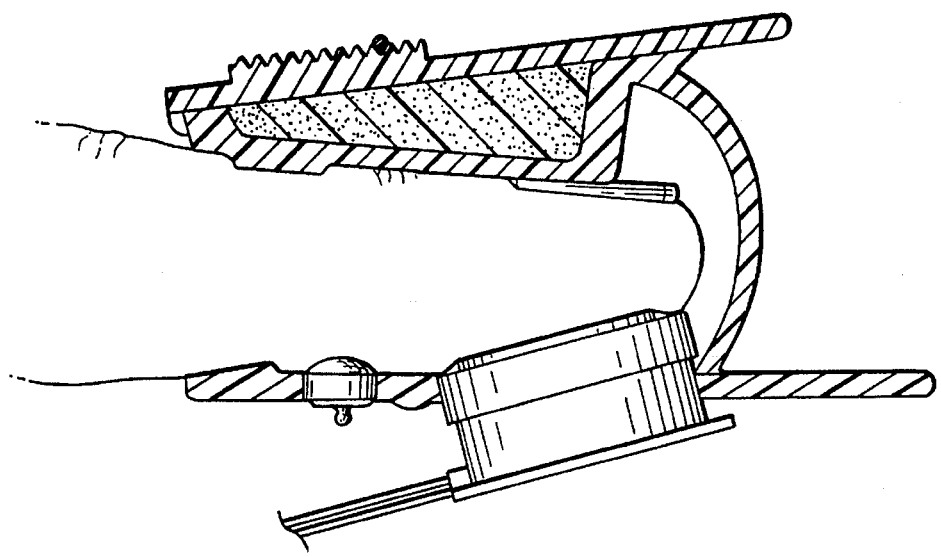
FIG. 11 is a cross sectional view along lines 11—11 of FIG. 10.
Figure 10:
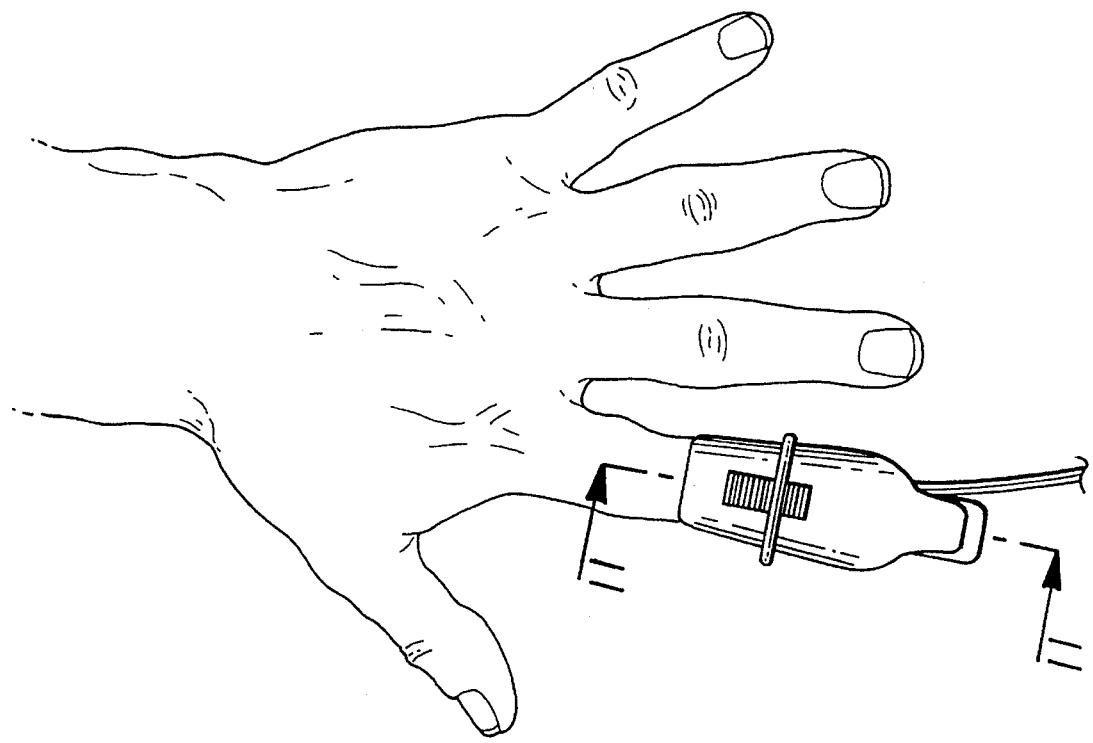
FIG. 10 is a top plan view of the finger monitoring device of the present invention.

Depending from the concave interior surface 122 of the upper arm 112 is a supporting member 124. The supporting member 124 is angled and increases in slope in the direction of the proximal end 120 to the distal end 118 of the upper arm 112 as shown in FIG. 11. The supporting member 124 has a concave bottom surface 126 that corresponds and conforms to the external curvature of a finger F. The supporting member 124 functions to cradle and support the top or dorsal surface of the finger F.

Figure 14:
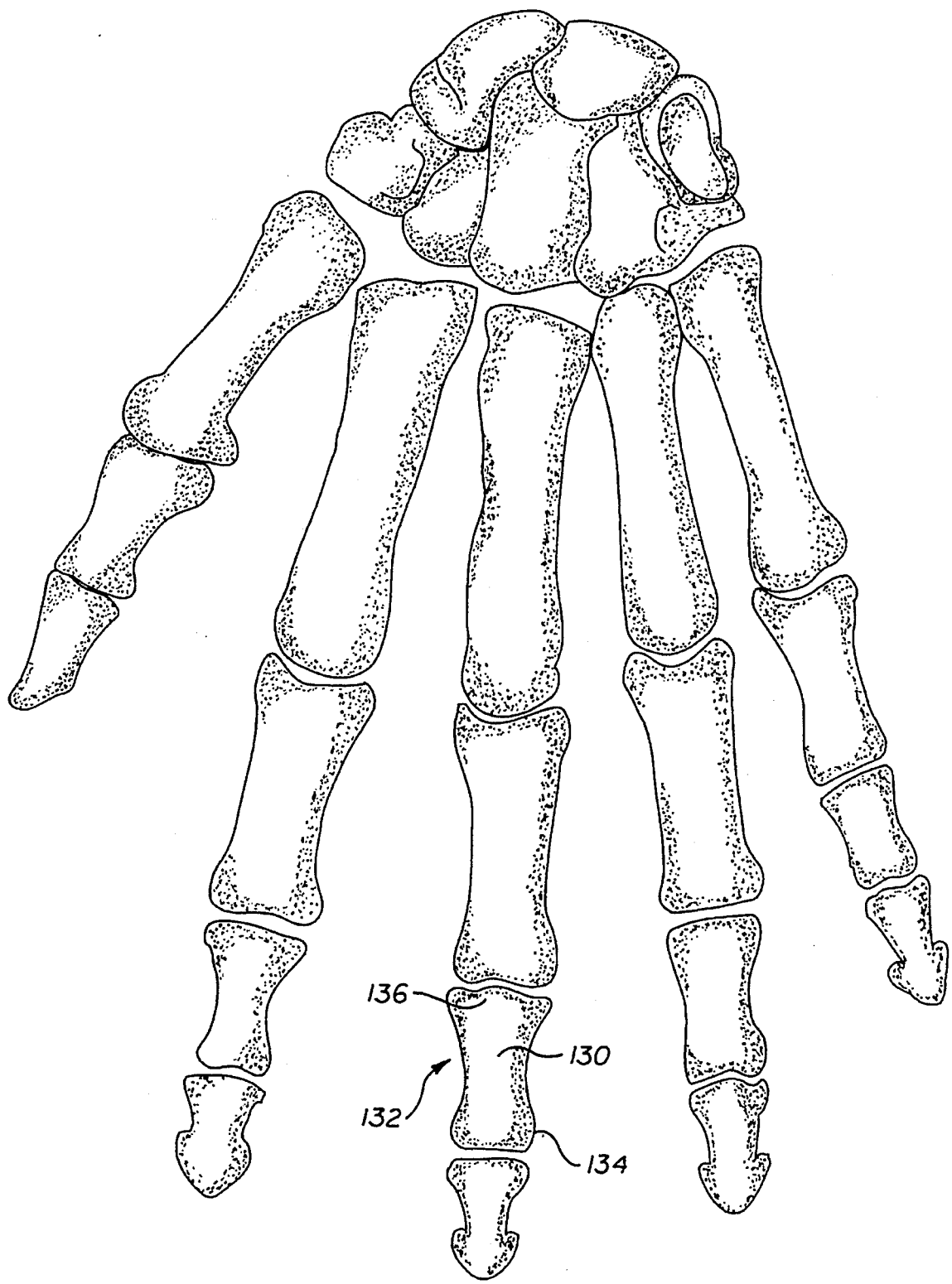
FIG. 14 is a top plan view of the dorsal surface of the bones in a human hand.

Protruding downward from the supporting member 124, near the middle of the concave bottom surface 126, is a rigid bone engaging member 128. In the preferred embodiment, the bone engaging member 128 is rectangular and is approximately ¾ inches long and ⅜ inches wide and about ⅛ inches thick and the bone engaging member 128 is made of a rigid material but is coated with a soft material such as foam rubber so as not to damage the finger F. The bone engaging member 128 is positioned so that when a finger F is placed within the finger attachment assembly 110, the bone engaging member 128 is located directly above the middle portion 130 of the middle phalanx 132 of the finger F as shown in FIG. 6. Referring to FIG. 14, the middle phalanx 132 is essentially a cylinder which is gently flared at both ends, the head 134 and the base 136, so that it presents a longitudinal concavity when viewed from the side. The bone engaging member 128 fits between the head 134 and the base 136 of the middle phalanx and presses against the middle portion 130 so that the finger F is stabilized within the finger attachment assembly 110 when the finger attachment assembly 110 is secured to the finger F. The middle portion 130 between the head 134 and base 136 is less innervated and therefore is less sensitive than the rest of the middle phalanx and thus reducing any pain sensation and any discomfort to the user that may result from use of the finger attachment assembly.

Referring back to FIG. 5, the lower arm 114 is a mirror image of the upper arm 112 and has the same overall dimensions as the upper arm 112. The lower arm 114 of the finger attachment assembly has a convex outer surface 138 and a concave inner surface 140 that corresponds and conforms to the external curvature of the finger F. The concave inner surface 140 has a padding means 142 near its proximal end 144 for supporting the lower surface of the finger F. The padding means 142 conforms to the curvature of the concave inner surface 140 of the lower arm 114 and is made of a soft padding material such as foam rubber to prevent irritation to the skin of the user. The padding means 142 is approximately ½ inches long and approximately ⅜ inches wide. The padding means 142 and the bone engaging member 128 work in conjunction with each other to firmly hold the finger F in place when the finger attachment assembly 110 is secured to the finger F as shown in FIGS. 6 and 11.

Referring to FIG. 6, located just distal to the padding means 142 is a first aperture 146 in the lower arm 114 for receiving and holding a first sensing monitor assembly 154. The first aperture extends through the lower arm 114 has a diameter of approximately ½ inches.

Pivotally mounted to the lower arm 114 and located just distal to the first aperture 146 is a spring means 148. Located on the convex exterior surface 123 of the upper arm 112 is a spring engaging member 150 having a series of evenly spaced ridges 152 for engaging and interlocking the end 151 of the spring means 148 used to tighten and fasten the finger attachment assembly 110 onto the finger F of the patient. The spring means 148 pivots about the lower arm 114 and the upper arm 112 to engage the ridges 152 of the spring engaging member 150 and fasten the finger attachment assembly 110 by clasping the upper arm 112 and the lower arm 114 against the finger F interposed therebetween. The tension applied by the spring means 148 to the finger attachment assembly 110 is adjusted by selecting one of the ridges 152 to which the spring means 148 is engaged appropriate for the desired finger size.

Referring back to FIG. 5, located distally to the first aperture 146 is a second aperture 156 for receiving and holding a second sensing monitor assembly 158. The second aperture 156 has a diameter of approximately ⅞ inches and extends through the lower arm 114 and is positioned so that a second sensing monitor assembly 158 is placed directly under the tip of finger F.

Figure 8:
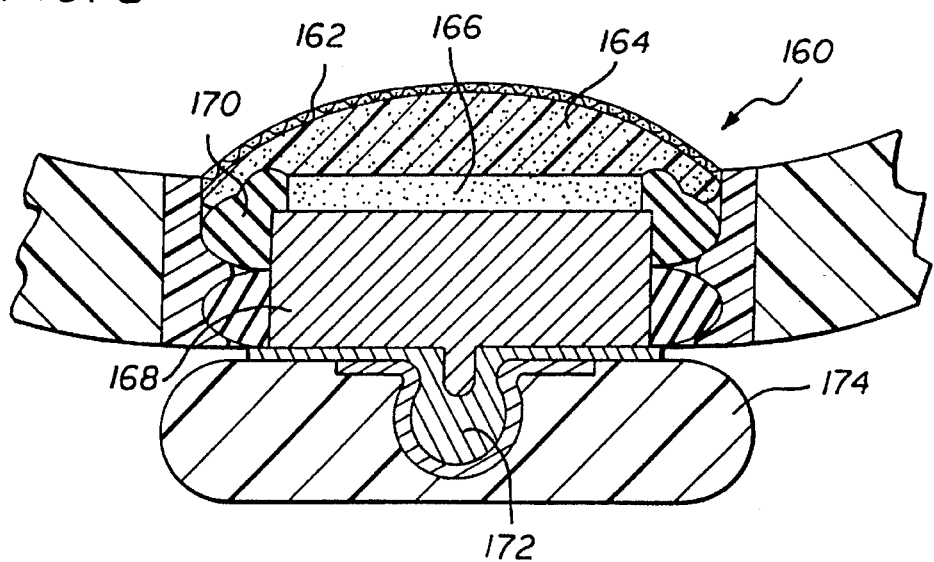
FIG. 8 is a cross sectional view along lines 8—8 of FIG. 7.

In the preferred embodiment of the present invention, the first sensing monitor assembly 154 comprises an improved electrode 160 for monitoring and recording the electrocardiogram of a patient. Referring to FIG. 8, the electrode 160 has a porous nylon sponge shield 162 as its outer surface, a high density sponge layer 164 providing cushion to the finger F of the patient, an antiseptic electroconductive gel bridge 165, a silver-silver chloride electrode 168, and a neoprene interface 170 for removably engaging the electrode 160 to the finger attachment assembly 118. An electrode projection 172 push fits into an electrode connector 174 so that the electrode 160 may be connected to recording equipment by an electrode lead 175.

The electrode 160 possesses the electrical advantages of a silver-silver chloride system without the adhesion problems as it is held in place within the first aperture 146 of the finger attachment assembly 110. This is of importance, especially during exercise where the adhesive system may weaken. With the electrode 160 of the present invention, the increased production of electrolyte-rich body fluids enhances the electrolytic efficiency of the conductive gel bridge 165 without lessening patient skin contact since the integrity of the skin-electrode coupling is dependent on mechanical coupling rather than an adhesive one.

Furthermore, the electrode 160 is so constructed that it is reusable. Cross-infection is largely eliminated by the use of an antiseptic conductive gel between the patient and the electrode 160. Additionally, between uses, the electrode 160 can be immersed in an antiseptic solution, without compromising electrical performance.

Figure 9:
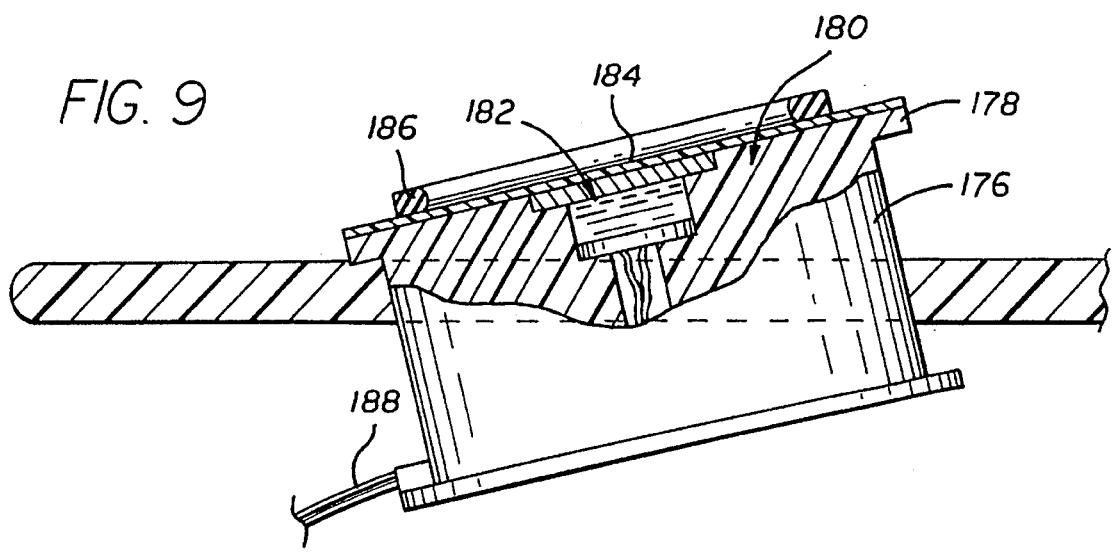
FIG. 9 is a cross sectional view along lines 9—9 of FIG. 7.

Referring to FIG. 9, in the preferred embodiment, the second sensing monitor assembly 158 comprises a housing 176 having a head portion 178 having an outer diameter larger than the diameter of the second aperture 156. The housing 176 has a longitudinal opening 180 for receiving a transducer 182, which is responsive to pressure applied to a lowered active surface 184. The transducer 182 may be any of the well-known pressure transducers as described in U.S. Pat. No. 4,993,422, issued Feb. 19, 1991 to Hon et al. and are incorporated herein by reference. The second sensing monitor assembly 158 has fixed around and below the lowered active surface 184 of the transducer 182 an isolation ring 186 that causes a small portion of the skin in the tip of the finger F to be formed into a dome that is brought into contact with the active surface 184 of the transducer 182. This permits a uniform surface to be presented to the transducer 182.

The active surface 184 of the transducer 182 should be substantially smaller than the inside diameter of the isolation ring 186 so as to permit the tissue to form a dome and not cause the tissue to flatten. The width of the isolation ring 186 is small in relationship to its inside diameter. The small width of the isolation ring 186 prevents flattening of the tissue, while at the same time promotes the formation of the domed portion of tissue within the isolation ring 186.

In the preferred embodiment of the invention the outside diameter of the isolation ring 186 is ¾ inches and has a width of about 1/32 inches. The diameter of the active surface 184 of the transducer 182 is 3/16 inches. The isolation ring 186 extends about ⅛ inches below the active surface 184 of the transducer 182. This promotes tight mechanical coupling between the domed portion of the tissue and the active surface 184 of the transducer 182. The output from the transducer 182 is connected by a wire 188 to conventional analog recording equipment. Further, in the preferred embodiment the second sensing monitor assembly 158 is held at an angle with respect to the lower arm 114 as shown in FIG. 9.

Figure 12:
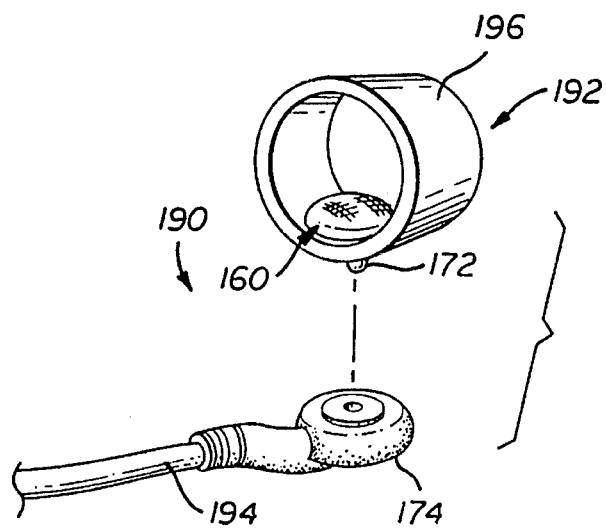
FIG. 12 is a perspective side view of the ring electrocardiograph electrode of the present invention.

Referring to FIG. 12, the third sensing monitor assembly 190 is a ring electrode 192 that is similar in construction to the electrode 160 described above but is removably attached by the neoprene interface 170 to a securing strap 196 in the shape of a ring for securing the ring electrode 192 to a finger F. The ring electrode 192 has a ring electrode lead 194 connected to the electrode connector 174 to connect the output from the ring electrode 192 to analog recording equipment. Typically, the ring electrode 192 is placed on a finger of the right hand of the patient while the finger attachment assembly 110 is placed on a finger of the left hand of the patient. In this manner, an electrocardiograph may be taken. The resultant electrocardiogram is equivalent to the widely used left arm-right arm lead system. If the ECG system requires an "indifferent" or "ground" electrode, the ring electrode 192 can be placed on another finger or on the same finger a distance apart (e.g. back and front). Such a ring electrode system provides a simple convenient easy-to-use method of obtaining a single lead ECG, moreover, it is especially useful for continuous monitoring of beat-to-beat rate and cardiac arrhythmia detection during diagnostic procedures and intensive care monitoring.

Referring to FIG. 11, the operation of the monitoring apparatus 100 is as follows: The fleshy portion of the patient's finger F is placed within the finger attachment assembly 110 with the finger nail facing upward, presenting the soft fleshy portion of the finger to the active surface 184 of the transducer 182. The upper arm 112 and the lower arm 114 are clasped together and held secure by the spring means 148 which has its end 151 secured to one of the ridges 152. In the clasped position, the bone engaging member 128 is positioned in the middle portion 130 of the middle phalanx 132 and the finger F is stabilized by the supporting member 124 and the padding means 142.

The wire 188 from the transducer 182 is connected to a conventional strip chart recorder for recording the changes in blood pressure obtained by the transducer 182. The electrode lead 175 and the ring electrode lead 194 are connected to an ECG recording device. A wrist securing assembly 200 having a band 202 secures the wire 188, the electrode lead 175, the ring electrode lead 194 and the equipment connector plug 204 to the wrist of the patient.

While the present invention has been described in detail with regards to the preferred embodiment, it is appreciated that other variations of the present invention may be devised which do not depart form the inventive concept of the present invention.

For example, instead of employing a pressure sensing device, other conventional sensory devices such as infra-red sensors may be employed which would indicate changes in the volume or pressure in the artery or other biophysical or biochemical function of the body without departing from the scope of the present invention.

What is claimed is:

1. A finger attachment assembly for measuring blood pressure comprising:

a first means for engaging the cylindrical dorsal surface of the finger;

a second means for engaging the palmside surface of the finger;

at least one blood pressure sensing and monitoring means for sensing and monitoring blood pressure;

means for holding and mechanically coupling to a finger said at least one blood pressure sensing and monitoring means; and at least one means for engaging the middle portion of the middle phalanx of the finger.

2. The apparatus of claim 1 in which said first means for engaging the dorsal surface of the finger includes an angled supporting member having a longitudinal concave bottom surface for engaging the cylindrical dorsal surface of the finger.

3. The apparatus of claim 2 in which said at least one means for engaging the middle portion of the middle phalanx is a bone engaging member protruding from said concave bottom surface.

4. The apparatus of claim 1 in which said second means for engaging the palmside surface comprises a padding means for supporting the palmside surface of the finger.

5. The apparatus of claim 1 in which said at least one means for engaging the middle portion of the middle phalanx comprises an electrode monitoring means for monitoring and recording the electrocardiogram of a patient.

* * * * *